United States Patent [19]

Wolvek

[11] Patent Number: 5,634,475
[45] Date of Patent: Jun. 3, 1997

[54] GUIDEWIRE DELIVERY ASSIST DEVICE AND SYSTEM

[75] Inventor: Sidney Wolvek, Brooklyn, N.Y.

[73] Assignee: Datascope Investment Corp., Montvale, N.J.

[21] Appl. No.: 299,071

[22] Filed: Sep. 1, 1994

[51] Int. Cl.⁶ ............................................. A61B 5/00
[52] U.S. Cl. ............................................. 128/772
[58] Field of Search .................... 128/657, 658, 128/772; 604/159, 171

[56] References Cited

U.S. PATENT DOCUMENTS

| | | | |
|---|---|---|---|
| 3,878,835 | 4/1975 | Utsugi | 604/159 |
| 4,860,757 | 8/1989 | Lynch et al. | 128/657 |
| 4,917,094 | 4/1990 | Lynch et al. | 128/657 |
| 4,957,117 | 9/1990 | Wysham | 128/772 |
| 5,137,288 | 8/1992 | Starkey et al. | 279/42 |
| 5,137,517 | 8/1992 | Loney et al. | 604/159 |
| 5,161,534 | 11/1992 | Berthiaume | 128/657 |
| 5,263,938 | 11/1993 | Orr et al. | 604/171 |
| 5,273,042 | 12/1993 | Lynch et al. | 128/657 |
| 5,273,052 | 12/1993 | Kraus et al. | 128/772 |
| 5,282,479 | 2/1994 | Havran | 128/772 |
| 5,312,338 | 5/1994 | Nelson et al. | 128/657 |
| 5,325,746 | 7/1994 | Anderson | 128/657 |
| 5,325,868 | 7/1994 | Kimmelstiel | 128/772 |
| 5,392,778 | 2/1995 | Horzewski | 128/657 |

OTHER PUBLICATIONS

"Super Arrow Flex™ Percutaneous Sheath Introduces Set With Integral Side Port/Hemostasis Value" (Arrow Product No. CP–07711; Product Brochure) (w/picture). May 1994.
"Olcott Torque Device", Cook Incorporated (product brochure; copyright 1992).

*Primary Examiner*—Max Hindenburg
*Attorney, Agent, or Firm*—Lerner, David, Littenberg, Krumholz & Mentlik

[57] ABSTRACT

A guidewire delivery assist device including a cylindrical body, having a lumen extending axially therethrough from a proximal end to a distal end thereof, for receiving a guidewire, and an integral grip. The grip includes a plurality of flexible grip members extending longitudinally through at least a portion of the cylindrical body and forming a plurality of internal surface portions defining a portion of the lumen of the cylindrical body. The grip members and interior surface portions are flexibly collapsible in a radial direction of the cylindrical body and a guidewire resident in the lumen of the cylindrical body is frictionally engageable by the internal surface portions.

30 Claims, 2 Drawing Sheets

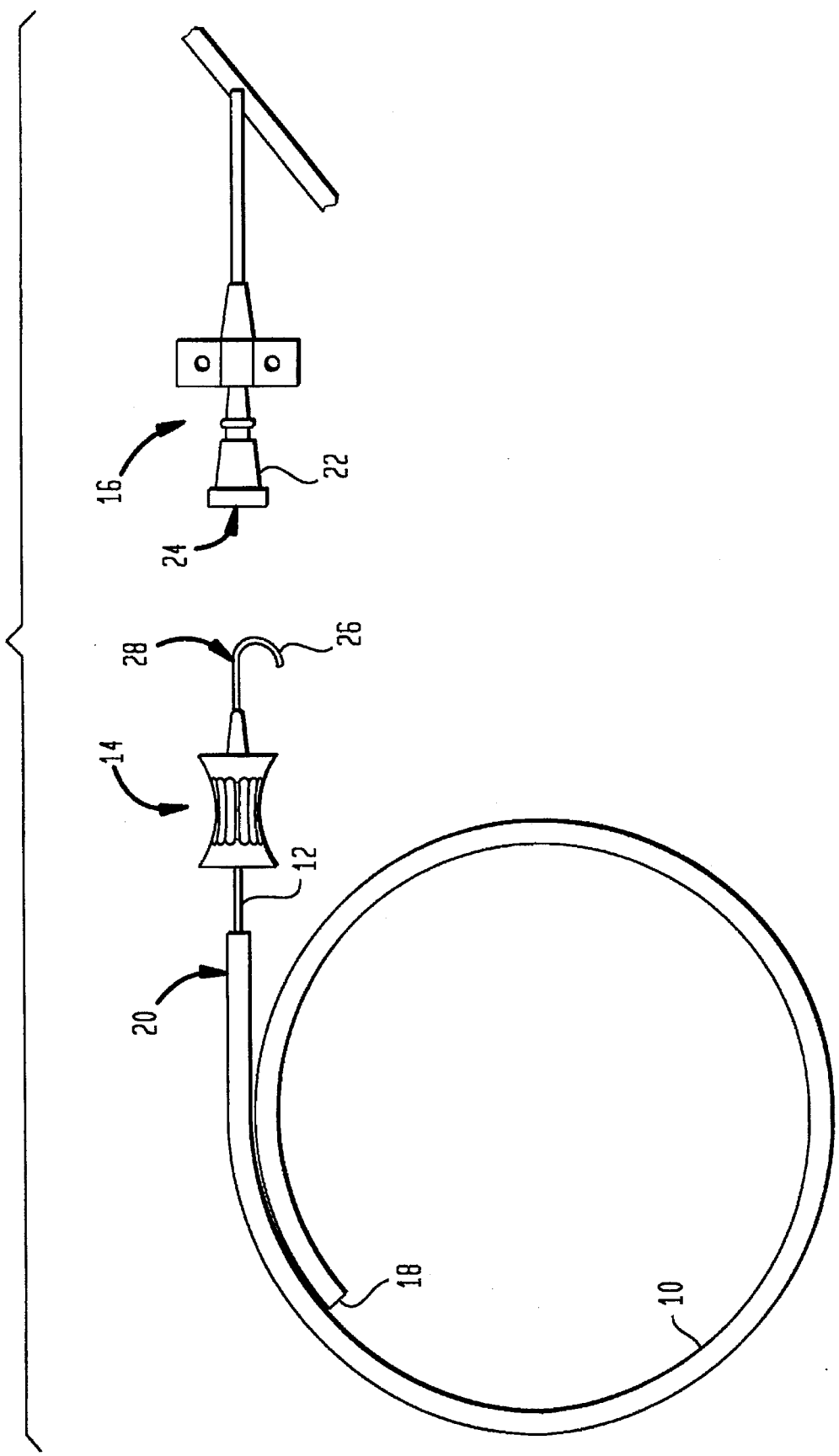

GUIDEWIRE DELIVERY ASSIST DEVICE AND SYSTEM

FIELD OF THE INVENTION

The present invention relates generally to medical procedures, and more particularly to a system and device for facilitating sterile and rapid introduction, insertion and manipulation of a guidewire for medical procedures. The system and device have particular utility in medical procedures such as balloon catheter angioplasty, intra-aortic balloon catheter cardiac assist procedures, and the like. However, the system and device may be used in any procedure that includes insertion and manipulation of a guidewire.

BACKGROUND OF THE INVENTION

Conventional medical procedures involving guidewire introduction, insertion and manipulation are well known. For example, a conventional method for angioplasty generally includes the steps of inserting a guidewire through an angiographic needle into the femoral artery, and digitally manipulating the external proximal end of the guidewire to advance the distal end of the guidewire through the patient's arterial tree, to the proximal aorta. A conventional percutaneous catheter, which generally has a much larger diameter than the guidewire, may then be easily and rapidly fed coaxially over the guidewire directly into the vasculature to perform an appropriate diagnostic or therapeutic procedure. Other medical procedures use similar guidewire introducing techniques for subsequently introducing, removing, or exchanging various catheters and like apparatus.

Insertion and manipulation of a guidewire in such procedures may be difficult and time consuming. Initially, guidewires have small diameters (e.g., 0.018 to 0.030 inch) and are extremely flexible. Thus, guidewires have a drawback in that they may bend and kink during insertion and manipulation. The incidence of kinking increases in procedures where the guidewire must be maneuvered through a diseased (sclerotic) portion of an artery, which may be hardened and include various obstructions, such as plaque.

Conventional guidewires typically are provided with a soft "J-tip". Specifically, the distal tip of the guidewire is made extremely flexible and is curved back upon itself to form a "J". This design has two advantages. First, it prevents punctures, e.g., piercing of the artery wall, by the sharp pointed guidewire during advancement. Second, the soft flexible distal end facilitates advancement in a snake-like movement. More particularly, advancement is achieved by a repeated combination of axial movement and torsional twisting generated at the externally exposed proximal end, to guide the soft flexible distal end through the arterial tree.

Such "J-tips" also have drawbacks. In particular, it is difficult for the clinician to insert the soft, flexible, curved distal tip into a small diameter guiding catheter, e.g., an angiographic needle.

Conventional guidewires also generally are provided with a protective coating, such as tetrafluoroethylene (Teflon™) or the like, which prevents blood from clotting on the guidewire and is biocompatible. However, such coatings have a drawback in that the coated guidewire becomes more slippery when wetted, particularly with blood. Thus, it is extremely difficult to accurately and precisely handle and manipulate (e.g., pinch and torque) these small diameter guidewires with the fingers. Such digital manipulation further is complicated when the clinician is required to wear latex gloves or the like, in order to maintain a sterile operating environment.

SUMMARY OF THE INVENTION

It is therefore an object of the present invention to provide an improved guidewire delivery system and method for facilitating rapid, reliable, and sterile storage, insertion and manipulation of a guidewire used in a medical procedure.

In one aspect, the present invention relates to a guidewire delivery assist device including a cylindrical body having a lumen extending axially therethrough, from a proximal end to a distal end thereof, for receiving a guidewire, and an integral grip including a plurality of flexible grip members extending longitudinally through at least a portion of the cylindrical body and forming a respective plurality of internal surface portions defining the lumen in that portion of the body, such that the flexible grip members and interior surface portions are flexibly collapsible in a radial direction of the cylindrical body, and a guidewire resident in the lumen of the cylindrical body is frictionally engageable by the internal surface portions.

In another aspect, the guidewire delivery assist device may include an integral guidewire straightener. In one embodiment, the straightener includes a conically shaped coaxial extension of the distal end of the delivery assist device, for facilitating initial insertion of the distal end of a guidewire into another catheter, such as an angiographic needle.

In yet another aspect, the present invention relates to a guidewire storage and delivery system including a guidewire housing, a guidewire, and a guidewire delivery assist device. The system may be prepackaged with the guidewire substantially resident in a lumen of the guidewire housing, and with a distal portion extending therefrom and resident in the lumen of the guidewire delivery assist device.

These and other objects, features and advantages of the present invention will become more apparent upon a consideration of the following description of the preferred embodiments of the present invention taken in conjunction with the accompanying drawings.

BRIEF DESCRIPTION OF THE DRAWINGS

FIG. 1 is an exploded perspective view of a guidewire delivery system utilizing a guidewire delivery assist device of the present invention.

DETAILED DESCRIPTION OF THE PREFERRED EMBODIMENTS

Figure 4:
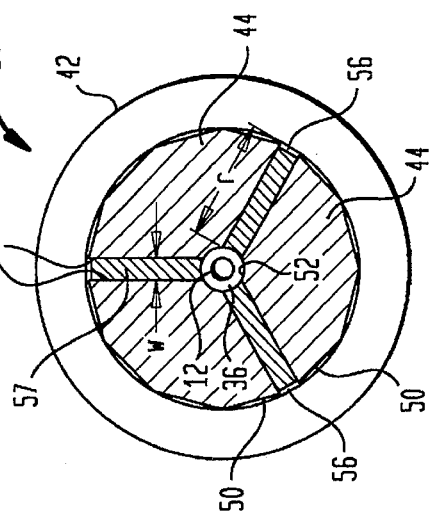
FIG. 4 is a cross-sectional view of an alternative embodiment of the device of FIG. 2.

Referring now to the drawings, wherein like reference numerals correspond to like or similar elements or features throughout the various figures, FIG. 1 illustrates in exploded view a system for guidewire storage, insertion and manipulation, including a guidewire delivery assist device of the present invention. As shown therein, the system generally comprises a housing 10 for storing a guidewire 12, a guidewire delivery assist device 14, and a catheter 16 (e.g., an angiographic needle). Although shown as a system in FIG. 1, it will be appreciated that these elements may be utilized independently. Accordingly, these elements may be provided individually or in any combination and subsequently assembled in various combinations or subcombinations.

Housing 10 generally may be any conventional guidewire housing. In the present embodiment, housing 10 is a conventional tubular housing, e.g. a helically coiled tube composed of a sterile, biocompatible plastic, such as polyethylene. The length and diameter of the tube, the number of turns, and the turn radius readily may be selected in accordance with the desired length and flexibility of guidewire 12, as is known in the art. Tubular housing 10 may be open at either or both of a proximal end 18 and a distal end 20 thereof. Tubular housing 10 also may be provided with conventional means (not shown) for advancing guidewire 12 out of distal end 20.

Likewise, catheter 16 may be any conventional catheter. Generally, catheter 16 is an insertion catheter suitable for facilitating percutaneous insertion of a guidewire 12 in a medical procedure. For example, as shown in the embodiment of FIG. 1 insertion catheter 16 may be an angiographic needle, such as a "Potts-Cournand" needle. As is known in the art, such a needle generally includes a fitting 22 at its proximal end, including an opening 24 having a conically shaped throat for facilitating initial placement of guidewire 12 into the lumen of angiographic needle 16.

Guidewire 12 may be any conventional guidewire, and preferable has a "J-tip" 26 at the distal end 28 thereof. Those skilled in the art readily will be able to select the desired length, diameter, and stiffness of guidewire 12 suitable for the intended medical procedure. Guidewire 12 also may include a protective coating that is biocompatible, such as tetrafluoroethylene (Teflon™), or the like, as is well known in the art.

Figure 2:
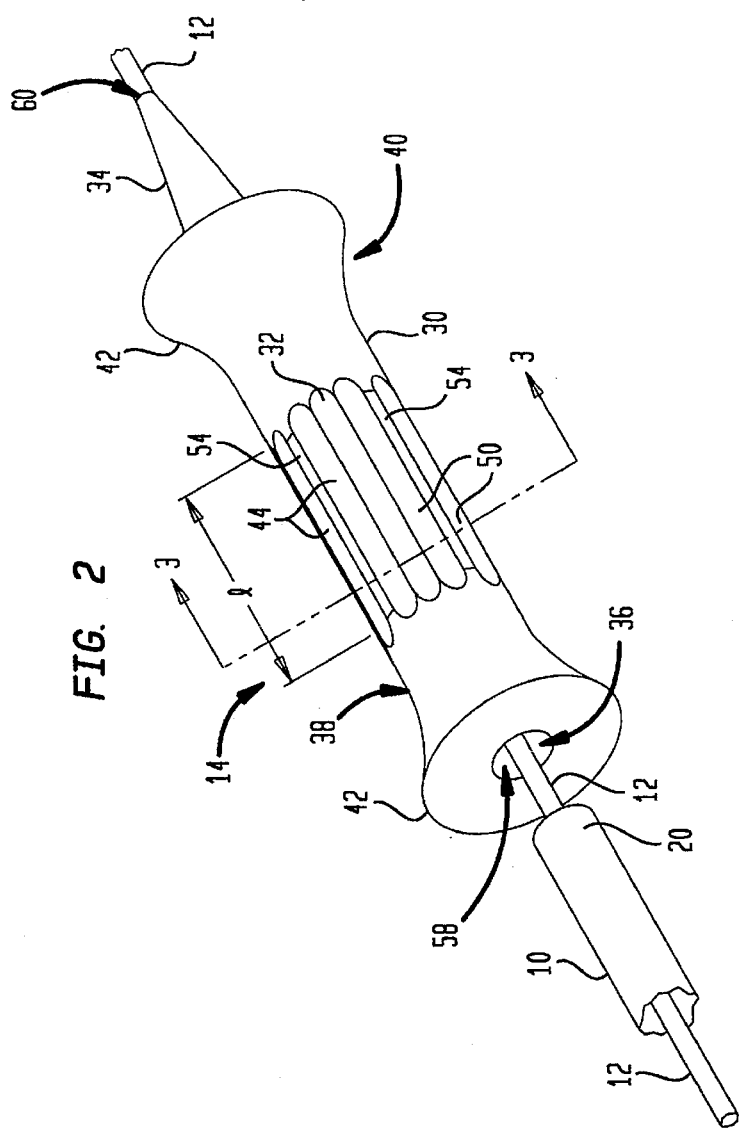
FIG. 2 is an exploded perspective view of a first embodiment of a guidewire delivery assist device of the present invention.

Referring now to FIGS. 1 and 2, guidewire delivery assist device 14 generally includes a cylindrical body 30, a grip 32, and an optional guidewire straightener 34.

As shown in FIGS. 1 and 2, cylindrical body 30 forms a lumen 36 therethrough from a proximal end 38 to a distal end 40, and preferably has a spool-like profile with flared or contoured proximal and distal ends. Specifically, each of proximal end 38 and distal end 40 preferably is provided with a contoured annular ridge 42. It will be appreciated that such contoured ends will provide for a firm, comfortable, no-slip grip, facilitate digital manipulation of the device in an axial direction.

In the present embodiment, body 30 is composed of a molded biocompatible plastic material, and grip 32 is provided integrally with body 30. As shown in FIGS. 1 and 2, grip 32 preferably is located in a central portion of body 30. However, it will be appreciated that grip 32 alternatively may be provided at proximal end 38 or distal end 40.

Figure 3:
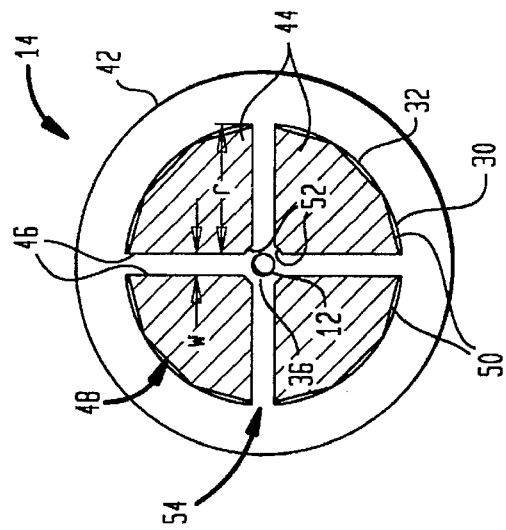
FIG. 3 is an enlarged cross-sectional view of a grip of the device of FIG. 2 taken along line 3—3.

Referring now to FIGS. 2 and 3, grip 32 generally includes a plurality of flexible, axially extending grip members 44. Each grip member 44 has a cross-section which forms an arcurate segment having two sides 46 extending substantially radially from lumen 36 of cylindrical body 30, and a generally arcurate exterior side 48. Exterior side 48 preferably includes facets 50, for facilitating gripping by fingers. As shown in FIG. 3, each grip member 44 also includes an internal surface portion 52, which, together with the internal surface portions of the other segments, defines a portion of lumen 36 of body 30.

The number and size (or relative size) of the grip members or segments 44 may vary, e.g., depending on the overall size of delivery assist device 14. In one embodiment, for example, as shown in FIG. 3, the number of grip members 44 may be an even number, and the grip members 44 may form a symmetrical pattern in cross-section. Specifically, grip 32 may include four segments or grip members 44.

Likewise, the number and size of facets 50 may vary, e.g., depending on the size of the segments. In the embodiment of FIG. 3, for example, each grip member 44 has three facets 50 formed on its arcuate exterior side 48.

It will be appreciated that such a symmetrical arrangement facilitates consistent, reliable handling. Specifically, the symmetrical arrangement of grip members 44 generally permits a guidewire 12 resident therein to be firmly gripped between at least two opposing internal surface portions 52.

As shown in FIGS. 2 and 3, grip members 44 are arranged so that a corresponding number of slits 54 respectively are formed between opposing interior sides 46 of adjacent grip members 44. Each slit 54 generally has an axial length "1", a width "w", and a radial length (or depth) "r". As discussed in greater detail below, this arrangement allows grip members 44 to flex and collapse radially inward when pinched between the fingers, so that a guidewire 12 resident in lumen 36 of body 30 may be gripped by opposing internal surface portions 52 of grip members 44.

The configuration of internal surface portions 52 also may vary. Generally, the cross-section profile is selected to provide a small clearance or tolerance gap between the internal surface portion 52 and a guidewire 12 resident in lumen 36. In this manner, it will be appreciated that delivery assist device 14 will float on guidewire 12 in an axial direction to enable the advancement of the guidewire into the body.

FIG. 4 illustrates in cross-section an alternative embodiment of a grip 32 of the present invention. As shown in FIG. 4, grip 32 may include an odd number of grip members or segments 44, e.g. three. As in the embodiment of FIGS. 2 and 3, the segments 44 of FIG. 4 may be symmetrically arranged. However, the relative size and geometry of the segments may be varied to suit a particular application. Likewise, each segment 44 may have a symmetrical arrangement of facets 50, e.g. four. However, the number and relative size of the facets 50 also may be varied to suit a particular application.

Those skilled in the art readily will be able to select the appropriate number and size of segments and facets sufficient to enable grasping, gripping and application of torsion with the fingers (even with wet gloves) for any desired application.

In another aspect, as also generally shown in FIG. 4, grip 32 may include pliable filler means located in the slits 54 between adjacent grip members 44. For example, grip 32 may include one or more connecting membranes 56 between adjacent grip members 44, e.g., at the radial periphery thereof, thereby covering slits 54. Membranes 56 may be formed by a thin film formed around the radial periphery of grip 32. Alternatively, or in addition, a soft, sponge-like filler material 57 may be disposed within slits 54, which permits grip members 44 to flex radially inward. It will be appreciated that this embodiment provides an additional safety feature, in that slits 54 are closed to the exterior environment, and any contaminants that may exist in the environment, e.g., on the clinicians fingers, are not transmitted through slits 54 to a guidewire 12 resident therein. In this manner, the guidewire delivery assist device 14 of the present invention further promotes sterile handling of guidewire 12.

An optional guidewire straightener 34 is provided at distal end 40 of body 30. Straightener 34 preferably has a conical body extending coaxially from body 30 and includes a coaxial lumen 60 for receiving guidewire 12. As is known in the art, guidewire straightener 34 may be used to temporarily straighten the "J-tip" 26 of a guidewire 12 resident therein, to facilitate initial insertion of guidewire 12 into another catheter or device, such as angiographic needle 16.

In a preferred method for using the guidewire delivery assist device of the present invention, a guidewire storage and delivery system is prepackaged including tubular housing 10, guidewire 12, and guidewire delivery assist device 14 (See, e.g., FIG. 1). Guidewire delivery assist device 14 is provided with a recessed port 58 at proximal end 38 forming connector means for removably accommodating distal end 20 of tubular housing 10. Alternatively, delivery assist device 14 may be provided integrally at the distal end 20 of housing 10. Guidewire 12 preferably is resident in tubular housing 10, with a distal portion 28 of guidewire 12 resident in lumen 36 of guidewire delivery assist device 14. The system may be prepackaged, e.g., in shrinkwrap plastic, as is well known in the art. It will be appreciated that such prepackaging provides for compact, sterile storage of the guidewire delivery system and guidewire 12.

When guidewire insertion is desired during a medical procedure, the prepackaging quickly may be discarded in the medical theater, thereby maintaining the system sterile prior to use. The clinician then pinches opposing grip members 44 of grip 32 between the fingers, to flex and collapse grip members 44 in a radial direction. In this manner, internal surface portions 52 frictionally engage or grasp guidewire 12, for example, between opposing internal surface portions 52. The clinician then may axially displace guidewire 12 (e.g., pull guidewire 12 from distal end 20 of tubular housing 10), rotate guidewire 12 about its axis (i.e., twist or torque guidewire 12), or both, by selectively pinching and sliding or manipulating guidewire delivery assist device 14 between the fingers.

By holding guidewire delivery assist device 14 between the fingers with reduced or no radial pressure, grip members 44 will return to an unflexed state, such that lumen 36 is unconstricted, and the clinician then may slide the delivery assist device 14 in an axial direction relative to guidewire 12 in order to advance the wire.

In one aspect, for example, the clinician may slide the delivery assist device 14 toward distal end 28 of guidewire 12. In this manner, it will be appreciated that J-tip 26 of guidewire 12 will be caused to straighten out while resident in lumen 60 of straightener 34. The clinician then may insert straightener 34, e.g., into conically shaped throat (opening) 24 of fitting 22 of an insertion catheter (angiographic needle) 16, to facilitate insertion of guidewire 12 into the lumen of the insertion catheter 16.

Further insertion of guidewire 12 through insertion catheter 16 may be achieved by repeated, reciprocal axial movement of delivery assist device 14 relative to guidewire 12, where the clinician applies radially inward pressure to grip members 44 when moving grip 32 in one axial direction, and releases radial pressure to grip members 44 when moving grip 32 in the opposite axial direction. It also will be appreciated that the contoured proximal and distal ends of spool-shaped body 30 facilitate free sliding axial movement of delivery assist device 14 relative to guidewire 12.

Further insertion of guidewire 12, e.g., through the patient's arterial tree, may be achieved by repeated, reciprocal movement alone or in combination with a twisting or torquing of delivery assist device 14 when grip members 44 are flexed to frictionally engage or grasp guidewire 12. In this manner, distal end 28 of guidewire 12 may be snaked through the arterial tree by digital manipulation of the exterior proximal end of guidewire 12.

Although the present invention has been described with respect to several specific embodiments and applications, it is not limited thereto. Numerous variations and modifications readily will be appreciated by those skilled in the art and are intended to be included within the scope of the present invention, which is recited in the following claims.

What is claimed is:

1. A guidewire delivery assist device, comprising;
  a generally cylindrical single-piece body having a lumen extending axially therethrough from a proximal end to a distal end for receiving a guidewire, said cylindrical body comprising an integral grip including a plurality of flexible grip members extending longitudinally through at least a portion of the cylindrical body and forming a respective plurality of internal surface portions defining a portion of the lumen such that the flexible grip members and respective internal surface portions are flexibly collapsible in a radial direction of the cylindrical body, and a guidewire resident in the lumen of the cylindrical body is frictionally engageable by said internal surface portions.

2. A device as recited in claim 1, wherein said grip is located in a central portion of said cylindrical body.

3. A device as recited in claim 1, wherein said flexible grip members are defined by a plurality of longitudinal slits in the cylindrical body.

4. A device as recited in claim 2, wherein said flexible grip members are defined by a plurality of longitudinal slits in the cylindrical body.

5. A device as recited in claim 1, wherein the number of grip members is three.

6. A device as recited in claim 1, wherein the number of grip members is four.

7. A device as recited in claim 1, said cylindrical body further comprising a tapered portion extending coaxially from the distal end thereof and having a lumen therethrough in communication with the lumen of the cylindrical body, for facilitating insertion of a guidewire resident in the lumen of the cylindrical body into a lumen of another apparatus.

8. A device as recited in claim 7, wherein said tapered portion has a conical taper.

9. A device as recited in claim 1, said cylindrical body further comprising contoured grip means located at at least one of the distal end and the proximal end of the cylindrical body.

10. A device as recited in claim 9, wherein said cylindrical body comprises contoured grip means located at each of the distal end and the proximal end of the cylindrical body.

11. A device as recited in claim 9, wherein said contoured grip means comprises an annular ridge.

12. A device as recited in claim 10, wherein said contoured grip means comprises an annular ridge located at each of the distal end and the proximal end.

13. A device as recited in claim 1, wherein said grip has a faceted exterior surface and a polygonal cross-section.

14. A device as recited in claim 2, wherein said grip has a faceted exterior surface and a polygonal cross-section.

15. A device as recited in claim 1, wherein said flexible grip members are defined by a plurality of longitudinal recesses in the cylindrical body.

16. A device as recited in claim 1, wherein said flexible grip members are defined by a plurality of longitudinal voids in the cylindrical body.

17. A guidewire delivery system, comprising a housing for storing a guidewire, said housing having a proximal end, a distal end, and an outlet at the distal end; and a guidewire delivery assist device comprising a generally cylindrical single-piece body having a lumen extending axially therethrough from a proximal end to a distal end for receiving a guidewire, said cylindrical body comprising an integral grip including a plurality of flexible grip members extending longitudinally through at least a portion of the cylindrical body and forming a respective plurality of internal surface portions defining a portion of the lumen such that the flexible grip members and respective internal surface portions are flexibly collapsible in a radial direction of the cylindrical body, and a guidewire resident in the lumen of the cylindrical body is frictionally engageable by said collapsible internal surface portions.

18. A system as recited in claim 17, further comprising a guidewire resident in at least said housing.

19. A system as recited in claim 17, said cylindrical body further comprising connector means for connecting a proximal end of the guidewire delivery assist device to the distal end of said tubular housing, such that a lumen of the connector is coaxial with, and communicates with, the outlet of the housing and the lumen of said cylindrical body.

20. A system as recited in claim 17, wherein said grip is located in a central portion of said cylindrical body.

21. A system as recited in claim 17, wherein said flexible grip members are defined by a plurality of longitudinal slits in said cylindrical body.

22. A system as recited in claim 17, wherein the number of grip members is three.

23. A system as recited in claim 17, wherein the number of grip members is four.

24. A system as recited in claim 17, said cylindrical body further comprising a tapered portion extending coaxially from the distal end thereof and having a lumen therethrough in communication with the lumen of the cylindrical body, to facilitate insertion of a guidewire resident in the lumen of the cylindrical body into a lumen of another apparatus.

25. A system as recited in claim 24, wherein said tapered portion has a conical taper.

26. A system as recited in claim 17, said cylindrical body further comprising contoured grip means located at at least one of the distal end and the proximal end of the cylindrical body.

27. A system as recited in claim 17, wherein said cylindrical body comprises contoured grip means located at each of the distal end and the proximal end of the cylindrical body.

28. A system as recited in claim 26, wherein said contoured grip means comprises an annular ridge.

29. A system as recited in claim 27, wherein said contoured grip means comprises an annular ridge located at each of the distal end and the proximal end.

30. A system as recited in claim 17, wherein said grip has a faceted exterior surface and a polygonal cross-section.

* * * * *